US005558873A

United States Patent [19]
Funk et al.

[11] Patent Number: 5,558,873
[45] Date of Patent: Sep. 24, 1996

[54] SOFT TISSUE CONTAINING GLYCERIN AND QUATERNARY AMMONIUM COMPOUNDS

[75] Inventors: Barbara S. Funk, Weyauwega; Duane G. Krzysik, Appleton; Patrick A. Pazdernik, Neenah, all of Wis.

[73] Assignee: Kimberly-Clark Corporation, Neenah, Wis.

[21] Appl. No.: 400,896

[22] Filed: Mar. 8, 1995

Related U.S. Application Data

[63] Continuation-in-part of Ser. No. 263,109, Jun. 21, 1994, abandoned.

[51] Int. Cl.⁶ ............................................... A01J 21/00
[52] U.S. Cl. ........................... 424/401; 252/91; 252/8.61; 428/537.5; 424/402; 424/404; 510/137
[58] Field of Search ........................ 424/401, 402, 424/404; 162/111, 112, 158; 252/91; 428/537.5

[56] References Cited

U.S. PATENT DOCUMENTS

| | | | |
|---|---|---|---|
| 967,688 | 8/1910 | Titherley . | |
| 1,102,203 | 6/1914 | Scott . | |
| 1,687,625 | 10/1928 | MacKenzie . | |
| 1,687,643 | 10/1928 | Berliner . | |
| 1,775,998 | 9/1930 | Greenberg . | |
| 1,874,864 | 8/1932 | Bernstein . | |
| 1,935,170 | 11/1933 | Woody et al. | 92/41 |
| 1,950,957 | 3/1934 | Wilhelm | 167/84 |
| 2,046,763 | 7/1936 | Asnes | 91/68 |
| 2,106,096 | 9/1938 | Hoffman | 91/63 |
| 2,226,075 | 12/1940 | Rowe | 252/134 |
| 2,389,736 | 11/1945 | Muise | 252/91 |
| 2,665,528 | 1/1954 | Sternfield et al. | 51/185 |
| 2,840,080 | 6/1958 | Clark | 128/296 |
| 2,933,431 | 4/1960 | Sperouleas | 167/84 |
| 2,999,265 | 9/1961 | Duane et al. | 15/506 |
| 3,049,228 | 8/1962 | Burnett | 206/58 |
| 3,129,811 | 4/1964 | Williams | 206/46 |
| 3,138,533 | 6/1964 | Heim et al. . | |
| 3,150,049 | 9/1964 | Emory | 167/90 |
| 3,264,188 | 8/1966 | Gresham | 167/84 |
| 3,305,392 | 2/1967 | Britt | 117/154 |
| 3,567,118 | 3/1971 | Shepherd | 239/6 |
| 3,619,280 | 11/1971 | Scheuer | 117/154 |
| 3,619,842 | 11/1971 | Maierson | 15/104.93 |
| 3,691,270 | 9/1972 | Charle et al. | 424/28 |
| 3,728,213 | 4/1973 | Hinz | 162/161 |
| 3,776,773 | 12/1973 | Taft | 134/6 |
| 3,791,266 | 2/1974 | Bucalo | 93/1 R |
| 3,818,533 | 6/1974 | Scheuer | 15/104.93 |
| 3,823,057 | 7/1974 | Roberts et al. | 161/112 |
| 3,896,807 | 7/1975 | Buchalter | 128/261 |
| 3,950,578 | 4/1976 | Laumann | 427/378 |
| 4,112,167 | 9/1978 | Dake et al. | 428/154 |
| 4,426,418 | 1/1984 | Coleman et al. | 428/211 |
| 4,481,243 | 11/1984 | Allen | 428/154 |
| 4,486,374 | 12/1984 | Stelzer | 264/156 |
| 4,513,051 | 4/1985 | Lavash | 428/212 |
| 4,550,035 | 10/1985 | Smith | 427/398.1 |
| 4,572,915 | 2/1986 | Crooks | 514/458 |
| 4,657,691 | 4/1987 | Hara et al. | 252/91 |
| 4,659,573 | 4/1987 | Frischling et al. | 424/63 |
| 4,735,935 | 4/1988 | McAnalley | 514/53 |
| 4,806,418 | 2/1989 | Sigl | 428/284 |
| 4,816,320 | 3/1989 | St. Cyr | 428/198 |
| 4,839,162 | 6/1989 | Komori et al. | 424/63 |

(List continued on next page.)

FOREIGN PATENT DOCUMENTS

| | | |
|---|---|---|
| 508516 | 7/1979 | Australia . |
| 564042 | 4/1984 | Australia . |
| B3401184 | 5/1984 | Australia . |
| 566215 | 10/1987 | Australia . |
| A3892589 | 7/1989 | Australia . |
| 620748 | 6/1991 | Australia . |
| 644457 | 1/1992 | Australia . |
| A8484591 | 4/1992 | Australia . |
| 638399 | 6/1993 | Australia . |
| 644499 | 12/1993 | Australia . |
| 0032793 | 10/1984 | European Pat. Off. . |
| 0165696 | 12/1985 | European Pat. Off. . |
| 0191128 | 8/1986 | European Pat. Off. . |
| 0257824 | 3/1988 | European Pat. Off. . |
| 0524892 | 1/1993 | European Pat. Off. . |
| 2538238 | 6/1984 | France . |
| 2746098 | 4/1979 | Germany . |
| 8704537 | 7/1987 | Germany . |
| 3720232 | 7/1988 | Germany . |
| 3924898 | 1/1991 | Germany . |
| 53-147803 | 12/1978 | Japan . |
| 57-125726 | 8/1982 | Japan . |
| 59-16816 | 1/1984 | Japan . |
| 62-236516 | 10/1987 | Japan . |
| 63-162610 | 7/1988 | Japan . |
| 63-275311 | 11/1988 | Japan . |
| 274694 | 3/1990 | Japan . |
| 2182999 | 7/1990 | Japan . |
| 3182218 | 8/1991 | Japan . |
| 415021 | 1/1992 | Japan . |
| 520093 | 3/1993 | Japan . |
| 423912 | 4/1974 | U.S.S.R. . |
| 780443 | 7/1957 | United Kingdom . |
| 1127438 | 9/1968 | United Kingdom . |
| 1326080 | 8/1973 | United Kingdom . |
| 1591294 | 6/1981 | United Kingdom . |
| WO9305752 | 4/1993 | WIPO . |
| WO9316678 | 9/1993 | WIPO . |
| WO9402674 | 2/1994 | WIPO . |

OTHER PUBLICATIONS

Lammle, S., "Use of Glycerine as a Softener for Paper Products", *The World's Paper Trade Review*, Dec. 13, 1962, pp. 2050, 2052, 2054, 2056.

Pattison, E. Scott, "Glycerin in Paper Production", *Paper Trade Journal*. vol. 136, No. 11, Mar. 13, 1953, pp. 19–20.

*Primary Examiner*—James J. Bell
*Attorney, Agent, or Firm*—Gregory E. Croft

[57] ABSTRACT

A soft tissue having a soothing feel is disclosed which contains a softening composition comprising from about 20 to about 98 weight percent glycerin and from about 0.2 to about 5 weight percent of a selected quaternary ammonium compound.

14 Claims, No Drawings

U.S. PATENT DOCUMENTS

| | | | |
|---|---|---|---|
| 4,891,227 | 1/1990 | Thaman et al. | 424/443 |
| 4,891,228 | 1/1990 | Thaman et al. | 424/443 |
| 4,917,890 | 4/1990 | McAnalley | 424/195.1 |
| 4,950,545 | 8/1990 | Walter et al. | 428/446 |
| 5,085,856 | 2/1992 | Dunphy et al. | 424/64 |
| 5,179,128 | 1/1993 | Lyle et al. | 252/165 |
| 5,217,576 | 6/1993 | Van Phan | 162/158 |
| 5,223,096 | 6/1993 | Phan et al. | 162/158 |
| 5,227,242 | 7/1993 | Walter et al. | |
| 5,240,562 | 8/1993 | Phan et al. | 162/158 |
| 5,262,007 | 11/1993 | Phan et al. | 162/158 |
| 5,264,082 | 11/1993 | Phan et al. | 162/158 |
| 5,281,306 | 1/1994 | Kakiuchi et al. | 162/158 |
| 5,312,522 | 5/1994 | Van Phan et al. | 162/111 |
| 5,334,286 | 8/1994 | Van Phan et al. | 162/158 |

SOFT TISSUE CONTAINING GLYCERIN AND QUATERNARY AMMONIUM COMPOUNDS

This application is a continuation-in-part of U.S. patent application Ser. No. 08/263,109 filed Jun. 21, 1994, now abandoned.

BACKGROUND OF THE INVENTION

In the field of tissue development and production, considerable efforts have been directed toward improving the softness of the tissue. This has been approached in a variety of ways, generally by either improving the tissue basesheet or by adding chemicals to the tissue to provide improved feel. The addition of mineral oil or polysiloxanes, for example, are chemicals which provide a more smooth feel to the surface of the tissue. While the feel of the tissue is an important characteristic, the use of tissues offer an opportunity to provide other benefits to the user.

SUMMARY OF THE INVENTION

It has now been discovered that a superior soft tissue can provide a soothing feel by incorporating into the tissue an aqueous softening composition containing a combination of selected ingredients. In general, the invention resides in a tissue to which has been added an aqueous composition comprising glycerin and one or more particular organic quaternary ammonium compounds.

More specifically, the quaternary ammonium compound(s) can be selected from the group consisting of the following quaternary classes:

monoalkyl trimethyl quaternary amines having the following structure:

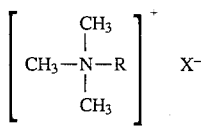

wherein X=chloride or methyl sulfate and R=aliphatic, saturated or unsaturated $C_{12}$-$C_{22}$;

benzyl quaternary amines having the following structure:

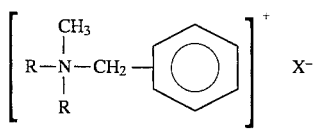

wherein X=chloride and R=aliphatic, normal $C_{12}$-$C_{18}$;

benzyl quaternary amines, such as stearalkonium chloride, having the following structure:

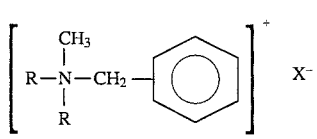

wherein X=chloride and R=straight chain $C_{18}$;

monomethyl trialkyl quaternary amines having the following structure:

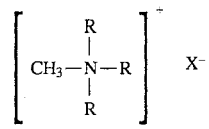

wherein X=chloride and R=aliphatic alkyl, normal or branched, $C_8$-$C_{18}$;

imidazolinium quaternary amines having the following structure:

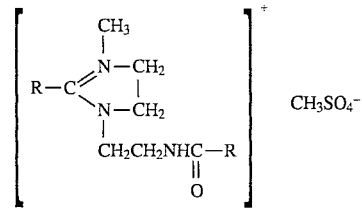

wherein X=methyl sulfate and R=aliphatic, normal, saturated or unsaturated, $C_{12}$-$C_{18}$;

silicone quaternary amines having the following structure:

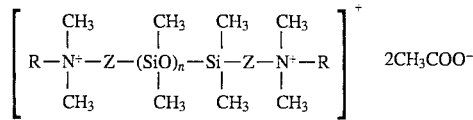

wherein

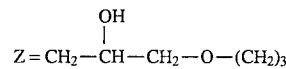

and R=long chain alkyl group, $C_{12}$-$C_{18}$; and quaternized lanolin derivatives, such as Quaternium-33, which have the following structure:

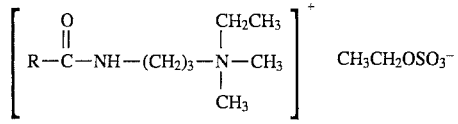

wherein RCO=lanolin acid radical.

The add-on amount of the softening composition can be from about 3 to about 30 dry weight percent based on the weight of the tissue, more specifically from about 3 to about 20 dry weight percent, and still more specifically from about 5 to about 15 dry weight percent. The higher add-on amounts are more likely to leave behind a detectable residue on the skin, whereas the lower add-on amounts are less likely to do so. Water can be added to the formulation to reduce the viscosity of the glycerin and to make the formulation more suitable for application.

The amount of the quaternary ammonium compound in the aqueous softening composition can be from about 0.2 to about 5 weight percent, more specifically from about 0.3 to about 3 weight percent, and still more specifically from about 0.5 to about 1 weight percent.

The amount of glycerin in the aqueous softening composition can be from about 20 to about 98 weight percent, more specifically from about 60 to about 80 weight percent, and still more specifically from about 40 to about 60 weight percent.

In addition, the softening composition can contain from about 0.5 to about 50 weight percent propylene glycol, more specifically from about 5 to about 30 weight percent propylene glycol. The propylene glycol can be used as a partial substitute for the glycerin in such formulations.

Also, the softening composition can contain from about 0.5 to about 50 weight percent polyethylene glycol, more specifically from about 5 to about 30 weight percent. The polyethylene glycol preferably has a molecular weight in the range of from about 200 to about 750. The polyethylene glycol can be used as a partial substitute for glycerin or propylene glycol in the softening composition.

Other optional ingredients include aloe, humectants, skin protectants, preservatives, and feel modifiers. Suitable humectants include lactic acid and its salts, sugars, ethoxylated glycerin, ethoxylated lanolin, corn syrup, hydrolyzed starch hydrolysate, urea, and sorbitol. Suitable skin protectants include allantoin, kaolin, and zinc oxide. Suitable feel modifiers include corn starch, oat flour, talc, boron nitride, and cyclodextrin.

The softening composition, which can be in the form of an aqueous solution or suspension, can be incorporated into the tissue by any suitable means such as spraying or printing onto the surface of the tissue.

The tissue to which the softening composition is applied can be any tissue useful as facial tissue, bath tissue, or towels. Such tissues can be produced by throughdrying or wet-pressing tissue making processes and can be creped or uncreped, layered or non-layered (blended).

EXAMPLES

Example 1

A solution consisting of 80 parts by weight glycerin and 19 parts by weight deionized water and 1 part aloe was prepared by mixing the three ingredients until uniform. The resulting solution was then applied to a three-ply, wet-pressed, creped tissue having a basis weight of about 45 grams per square meter using a spray apparatus. The add-on amounts included 5, 8, and 10 dry weight percent based on the weight of the tissue. The resulting tissue samples did not provide any unusual benefit.

Example 2

A softening composition consisting of 70 parts by weight glycerin, 19 parts by weight deionized water, 1 part by weight of Lanoquat 1751-A (a blend of Quaternium-33 (quaternized lanolin) and propylene glycol sold by Henkel Corporation, Ambler, Pa.) and 1 part by weight of aloe vera. The glycerin and Lanoquat 1751-A were mixed together first until uniform. Then the water and aloe vera was added and the mixture stirred until a homogeneous solution was achieved. The resulting softening solution was applied to a three-ply, wet-pressed, creped tissue having a basis weight of about 45 grams per square meter using a spray apparatus. The add-on amounts included about 10 and about 12 dry weight percent based on the dry weight of the tissue. The resulting tissue samples were unusually soft at both add-on levels.

Example 3

A softening composition was prepared consisting of 60 parts by weight glycerin, 20 parts by weight propylene glycol, 1 part by weight Lanoquat 1751-A, 19 parts by weight deionized water, and 1 part by weight aloe vera. The glycerin and propylene glycol were mixed together until uniform. The Lanoquat 1751-A was added and mixed until uniform. The water and aloe vera was then added and the solution was stirred until homogenous. The resulting softening composition was applied to a two-ply throughdried tissue having a basis weight of about 42 grams per square meter using a spray apparatus. The add-on amounts included 6, 9, and 12 dry weight percent based on the weight of the tissue. In addition, the resulting softening composition was applied to a four-ply, wet-pressed, creped tissue having a basis weight of about 45 grams per square meter using a spray apparatus. The add-on amounts included 6, 9, and 12 dry weight percent based on the weight of the tissue.

Example 4

A softening composition was prepared consisting of 60 parts by weight glycerin, 20 parts by weight propylene glycol, 5 parts by weight Lanoquat 1751-A, and 14 parts by weight deionized water, and 1 part by weight aloe vera. The glycerin and propylene glycol were mixed together until uniform. The Lanoquat 1751-A was added and mixed until uniform. The water and aloe vera was then added and the solution was stirred until homogeneous. The resulting softening composition was applied to a two-ply, throughdried creped tissue having a basis weight of about 42 grams per square meter using a spray apparatus. The add-on amounts included 6, 9, and 12 dry weight percent based on the weight of the tissue.

A sensory panel evaluated tissue samples from Example 3 and Example 4 versus an untreated two-ply, throughdried tissue, and a two-ply, throughdried tissue treated with a silicone at an add-on of 3 dry weight percent based on the weight of the tissue. The samples from Examples 3 and 4 were as good as or better for softness than the silicone-treated sample and better than the untreated control for softness. Example 4 with a 12 percent add-on had the best softness of all the samples, followed by Example 3 with a 12 percent add-on.

Example 5

A softening composition was prepared consisting of 40 parts by weight of propylene glycol, 1 part by weight of stearalkonium chloride, and 19 parts by weight of deionized water. The propylene glycol and the stearalkonium chloride were mixed together and heating until uniform. The glycerin was added and mixed until uniform. The water was then added and the solution was stirred until homogenous. The resulting softening composition was applied to a two-ply, throughdried, creped tissue having a basis weight of about 27 grams per square meter using a spray apparatus. The add-on amount was about 10 dry weight percent based on the weight of the tissue.

The tissue of Example 5 was evaluated subjectively by a sensory panel and found to be softer, silkier, and smoother than the samples of Example 3.

In all examples, except Example 1, as the add-on level increased, the resulting tissue became noticeably softer. The lower add-on levels produced tissues which did not leave a noticeable residue on the skin.

It will be appreciated that the foregoing examples, given for purposes of illustration, are not to be construed as limiting the scope of this invention, which is defined by the following claims and all equivalents thereto.

We claim:

1. An absorbent tissue to which has been added by spraying or printing on its surface from about 3 to about 30 dry weight percent of an aqueous softening composition, said softening composition comprising from about 20 to about 98 weight percent glycerin and from about 0.2 to about 5 weight percent of a quaternary ammonium compound selected from the group consisting of:

monoalkyl trimethyl quaternary amines having the following structure:

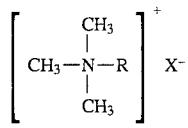

wherein X=chloride or methyl sulfate and R=aliphatic, saturated or unsaturated $C_{12}$-$C_{22}$;

benzyl quaternary amines having the following structure:

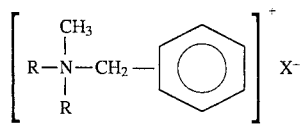

wherein X=chloride and R=aliphatic, normal $C_{12}$-$C_{18}$;

monomethyl trialkyl quaternary amines having the following structure:

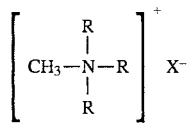

wherein X=chloride and R=aliphatic alkyl, normal or branched, $C_8$-$C_{18}$;

imidazolinium quaternary amines having the following structure:

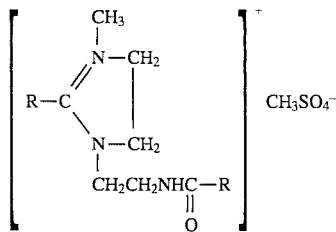

wherein X=methyl sulfate and R=aliphatic, normal, saturated or unsaturated, $C_{12}$-$C_{18}$;

silicone quaternary amines having the following structure:

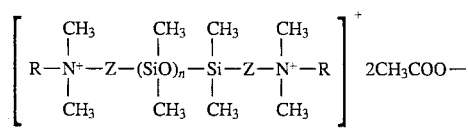

wherein

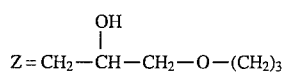

and R=long chain alkyl group, $C_{12}$-$C_{18}$; and quaternized lanolin derivatives which have the following structure:

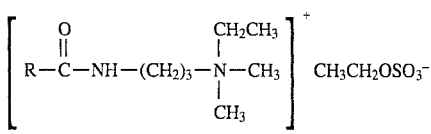

wherein RCO=lanolin acid radical.

2. The tissue of claim 1 wherein the quaternary ammonium compound is a monoalkyl trimethyl quaternary amine having the following structure:

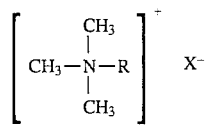

wherein X=chloride or methyl sulfate and R=aliphatic, saturated or unsaturated $C_{12}$-$C_{22}$.

3. The tissue of claim 1 wherein the quaternary ammonium compound is a benzyl quaternary amine having the following structure:

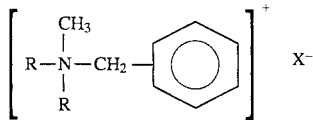

wherein X=chloride and R=aliphatic, normal $C_{12}$- $C_{18}$.

4. The tissue of claim 1 wherein the quaternary ammonium compound is a benzyl quaternary amine having the following structure:

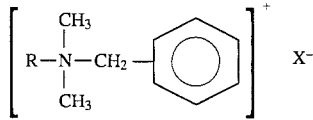

wherein X=chloride and R=straight chain $C_{18}$.

5. The tissue of claim 1 wherein the quaternary ammonium compound is a monomethyl trialkyl quaternary amine having the following structure:

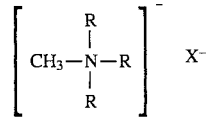

wherein X=chloride and R=aliphatic alkyl, normal or branched, $C_8$-$C_{18}$.

6. The tissue of claim 1 wherein the quaternary ammonium compound is an imidazolinium quaternary amine having the following structure:

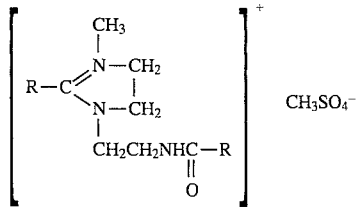

wherein X=methyl sulfate and R=aliphatic, normal, saturated or unsaturated, $C_{12}$-$C_{18}$.

7. The tissue of claim 1 wherein the quaternary ammonium compound is a silicone quaternary amine having the following structure:

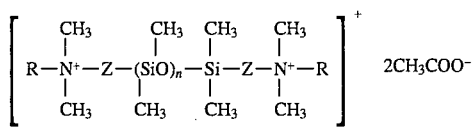

wherein

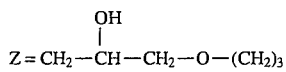

and R=long chain alkyl group, $C_{12}-C_{18}$.

8. The tissue of claim 1 wherein the quaternary ammonium compound is a quaternized lanolin derivative having the following structure:

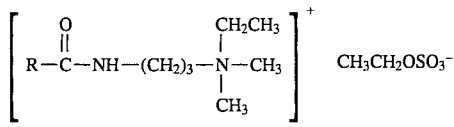

wherein RCO=lanolin acid radical.

9. The tissue of claim 1 wherein the softening composition further comprises from about 0.5 to about 50 weight percent propylene glycol.

10. The tissue of claim 1 wherein the softening composition further comprises from about 0.5 to about 50 weight percent polyethylene glycol.

11. The tissue of claim 1 further comprising a humectant selected from the group consisting of lactic acid and its salts, sugars, ethoxylated glycerin, ethoxylated lanolin, corn syrup, hydrolyzed starch hydrolysate, urea, and sorbitol.

12. The tissue of claim 1 further comprising a skin protectant selected from the group consisting of allantoin, kaolin, zinc oxide, and dimethicone emulsions, talc, and starch.

13. The tissue of claim 1 further comprising a feel-modifier selected from the group consisting of corn starch, oat flour, talc, boron nitride, and cyclodextrin.

14. A facial tissue comprising from about 5 to about 30 dry weight percent of a softening composition added to the surface of the tissue by spraying or printing, said softening composition comprising from about 60 to about 80 weight percent glycerin, from about 0.5 to about 20 weight percent propylene glycol, and from about 1 to about 4 weight percent of a quaternized lanolin having the following structure:

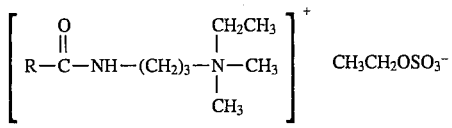

* * * * *